United States Patent
Suehara

(10) Patent No.: US 10,219,681 B2
(45) Date of Patent: Mar. 5, 2019

(54) ACTUATING MEMBER AND MEDICAL APPARATUS

(71) Applicant: Terumo Kabushiki Kaisha, Tokyo (JP)

(72) Inventor: Satoru Suehara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 521 days.

(21) Appl. No.: 14/871,399

(22) Filed: Sep. 30, 2015

(65) Prior Publication Data

US 2016/0015251 A1  Jan. 21, 2016

Related U.S. Application Data

(63) Continuation of application No. PCT/JP2013/059916, filed on Apr. 1, 2013.

(51) Int. Cl.
  *A61B 1/005* (2006.01)
  *A61M 25/01* (2006.01)
  (Continued)

(52) U.S. Cl.
  CPC .......... *A61B 1/0057* (2013.01); *A61B 1/0052* (2013.01); *A61B 17/3421* (2013.01);
  (Continued)

(58) Field of Classification Search
  CPC .......... A61M 25/0136; A61M 25/0138; A61M 25/0147; A61B 1/0057; A61B 1/0052;
  (Continued)

(56) References Cited

U.S. PATENT DOCUMENTS

2008/0139886 A1  6/2008  Tatsuyama
2009/0281619 A1*  11/2009  Le .......................... A61F 2/2433
                                                                 623/2.11
2011/0282176 A1*  11/2011  Tegg ..................... A61B 5/042
                                                                 600/374

FOREIGN PATENT DOCUMENTS

JP   H05-501065 A   3/1993
JP   2001-161636 A   6/2001
(Continued)

OTHER PUBLICATIONS

International Search Report dated Sep. 17, 2013 issued in PCT/JP2013/059916.

*Primary Examiner* — Kevin C Sirmons
*Assistant Examiner* — Leah Swanson
(74) *Attorney, Agent, or Firm* — Foley & Lardner LLP

(57) ABSTRACT

An actuating member, which makes a flexible elongated member for medical use perform a predetermined action, includes a push/pull member and an operating member. The push/pull member includes a first moving portion and a second moving portion which are disposed on a proximal side and are movable relative to each other, a first extending portion that extends from the first moving portion, and a second extending portion that extends from the second moving portion. The push/pull member is pushed/pulled in conjunction with a movement of the first moving portion and the second moving portion. The operating member is rotatable in a circumferential direction of the elongated member. The operating member includes a first guide portion and a second guide portion, which guide the first moving portion and the second moving portion. The push/pull member is capable of making the elongated member perform an advance/retraction action and/or a bending action.

19 Claims, 11 Drawing Sheets

(51) Int. Cl.
*A61B 17/34* (2006.01)
*A61B 17/00* (2006.01)
*A61B 90/00* (2016.01)

(52) U.S. Cl.
CPC .... *A61M 25/0136* (2013.01); *A61M 25/0138* (2013.01); *A61M 25/0147* (2013.01); *A61B 2017/00309* (2013.01); *A61B 2017/00327* (2013.01); *A61B 2090/3937* (2016.02)

(58) Field of Classification Search
CPC .......... A61B 17/3421; A61B 2017/003; A61B 2017/00318; A61B 2017/00323; A61B 2017/00327
USPC ....................................................... 604/95.04
See application file for complete search history.

(56) References Cited

FOREIGN PATENT DOCUMENTS

| | | |
|---|---|---|
| JP | 2001-516257 A | 9/2001 |
| JP | 2008-142199 A | 6/2008 |
| WO | WO-90/10417 A1 | 9/1990 |
| WO | WO-98/41276 A1 | 9/1998 |

\* cited by examiner

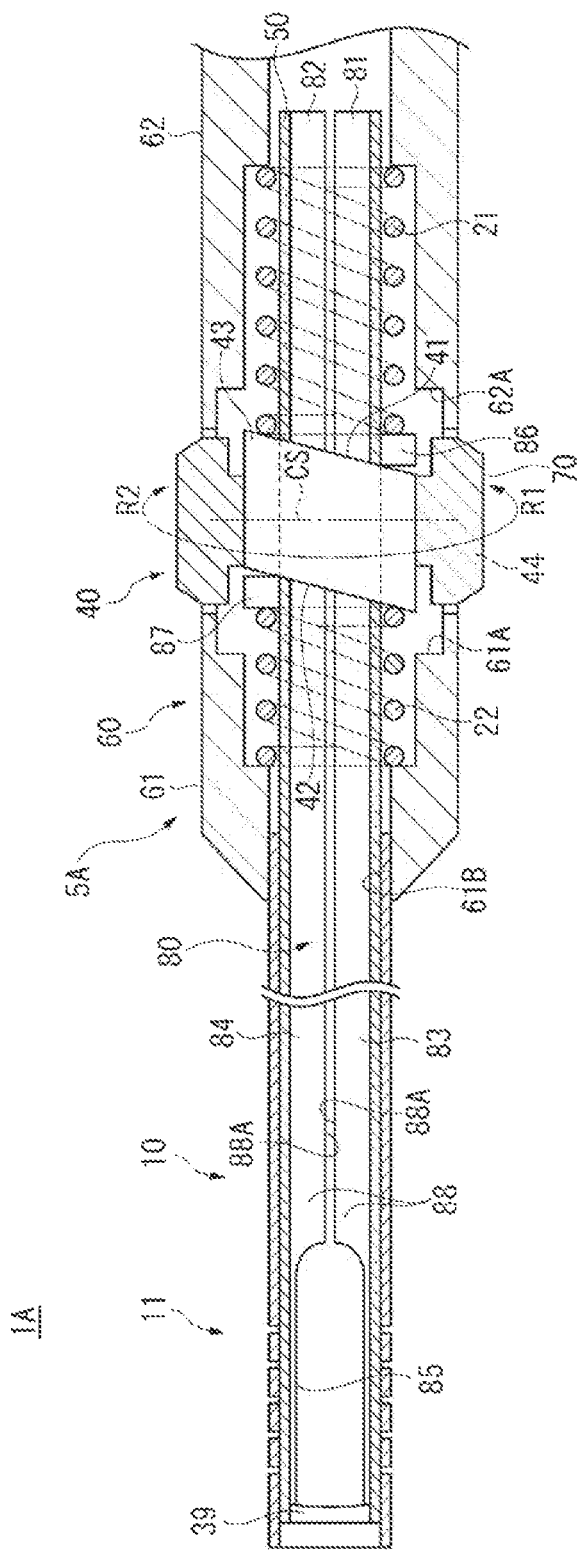

ACTUATING MEMBER AND MEDICAL APPARATUS

CROSS-REFERENCE TO RELATED PATENT APPLICATION

This application is a continuation application of and claims the benefit of priority from International Patent Application No. PCT/JP2013/059916, filed Apr. 1, 2013, the contents of which are incorporated herein by reference.

BACKGROUND

The present disclosure relates to an actuating member for making a medical elongated member perform a predetermined action, and a medical apparatus equipped with the actuating member.

In the medical field, a flexible elongated member is generally used as a medical apparatus for performing administration of medicine into a living body, suction or injection of various fluids, introduction of other medical apparatuses into the living body, or the like. For example, where an elongated member is used for the introduction of other medical apparatuses, prior to the introduction of the medical apparatus, the elongated member is inserted into a lumen (a blood vessel, a body cavity, or the like) of the living body and is guided to a target area, such as an area to be treated and its peripheral area. In order to appropriately guide the elongated member to the target area during such use, it is often necessary to introduce the elongated member along a curved path like the lumen of the living body. For this reason, the elongated member may include an actuating member capable of performing a bending operation by a user's proximal operation when the elongated member is used.

As to techniques related to this, Japanese Patent Laid-Open No. 2008-142199 (hereinafter referred to as "Patent Document 1") describes an actuating member including a push/pull member connected to an elongated member, a pulley around which the push/pull member is wound, and a handle for rotationally actuating the pulley, and an endoscope into which the actuating member is assembled. In the actuating member, the handle is arranged on a proximal side of the endoscope and rotates around an axis orthogonal to the axial direction of the elongated member, thereby winding the push/pull member to perform a bending action.

SUMMARY

In the actuating member of Patent Document 1, the push/pull member is arranged so as to be wound around the pulley and an action direction in which the push/pull member is pushed/pulled is converted from a straight direction into a circumferential direction for bending. Therefore, a wire with a relatively small rigidity or the like, is used as the push/pull member. For this reason, there is a possibility that a push/pull force cannot be reliably transmitted to the elongated member via this wire.

Additionally, because it is necessary to wind the wire around the pulley with good followability, the pulley must be large, causing the entire apparatus to be large.

Disclosed herein is an actuating member by which an advance/retraction movement of a push/pull member can be efficiently transmitted to an elongated member and which enables a smaller medical apparatus to be realized, and a medical apparatus equipped with the actuating member.

The object of certain embodiments of the present disclosure will be achieved by any one of the followings.

In one aspect, an actuating member for making a flexible elongated member for medical use perform a predetermined action includes a push/pull member and an operating member. The push/pull member includes a first moving portion and a second moving portion which are disposed on a proximal side in an axial direction of the elongated member and which are movable relative to each other in an axial direction of the elongated member. The push/pull member further includes a first extending portion that extends from the first moving portion toward a distal side in the axial direction of the elongated member and a second extending portion that extends from the second moving portion toward the distal side in the axial direction of the elongated member. The push/pull member is pushed/pulled in the axial direction of the elongated member in conjunction with a movement of the first moving portion and the second moving portion. The operating member, which effects the movement of the first moving portion and the second moving portion, is rotatable in a circumferential direction of the elongated member. The operating member includes a first guide portion, which is inclined against an orthogonal plane orthogonal to the axial direction of the elongated member and which guides the movement of the first moving portion, and a second guide portion, which is inclined against the orthogonal plane and which guides the movement of the second moving portion. The push/pull member is capable of making the elongated member perform at least one of (i) an advance/retraction action and (ii) a bending action, by transmitting the movement of the first moving portion and the second moving portion, which are guided by the first guide portion and the second guide portion, to the elongated member.

According to the actuating member configured as above, the push/pull member is pushed/pulled in the axial direction of the elongated member, without conversion of its action direction, and the elongated member is thereby made to perform an advance/retraction action or a bending action. Therefore, the advance/retraction movement of the push/pull member can be efficiently transmitted to the elongated member. In addition, since it is unnecessary to wind the push/pull member around the operating member, a medical apparatus reduced in overall size can be realized.

In the actuating member as above, the operating member may be configured to be capable of moving the first moving portion and the second moving portion in opposite directions along the axial direction, and the movement of the first moving portion and the second moving portion makes the elongated member perform the bending action.

According to this configuration, the first moving portion and the second moving portion are moved in the opposite directions, to thereby make the elongated member perform a bending action. Therefore, the elongated member can be bent with reduced traveling distances of the first moving portion and the second moving portion. Consequently, operability of the actuating member is enhanced.

In the actuating member as above, the operating member may be configured to be capable of moving the first moving portion and the second moving portion, with different traveling distances, in the same direction along the axial direction, and the movement of the first moving portion and the second moving portion makes the elongated member perform both the advance/retraction action and the bending action.

According to this configuration, the first moving portion and the second moving portion are moved in the same direction, thereby to make the elongated member perform a bending action. Therefore, the elongated member can perform a bending action while conducting an advance/retraction action. Thus, an actuating member with enhanced performance can be provided.

In the actuating member as above, the operating member may be composed of an annular member so designed that one of its end surface on one side in the axial direction, its end surface on other side in the axial direction, and a guide groove formed in its inner peripheral surface constitutes each of the guide portions. The first moving portion includes a first projection that makes contact with the first guide portion and the second moving portion includes a second projection that makes contact with the second guide portion. The movement of the first moving portion and the second moving portion can be effected by rotating the operating member.

According to this configuration, each of the projections of the first and second moving portions is preliminarily put in contact with one of the end surfaces of the operating member and the guide groove in the inner peripheral surface of the operating member, whereby the movement of the moving portions is realized. Therefore, the elongated member can be bent with a simple configuration, and a smaller medical apparatus can be realized.

In the actuating member as above, the operating member may be composed of a tubular member of which the one-side end surface constituting the first guide portion and the other-side end surface constituting the second guide portion are inclined against the orthogonal plane, the first projection makes contact with the one-side end surface, and the second projection makes contact with the other-side end surface.

According to this configuration, the first and second projections are preliminarily put in contact with the one-side end surface and the other-side end surface of the operating member, whereby the movement of the moving portions is realized. Therefore, moving characteristics of the moving portions in conjunction with the rotation of the operating member can be set by the profile of the end surfaces of the operating member. As a consequence, the degree of freedom in setting the bending of the elongated member can be enhanced with a simple configuration.

In the actuating member as above, the operating member may be composed of a tubular member which has its inner peripheral surface formed with a first guide groove constituting the first guide portion and with a second guide groove constituting the second guide portion, the first projection makes contact with the first guide groove, and the second projection makes contact with the second guide groove.

According to this configuration, the movement of each moving portion is realized through preliminary engagement of each corresponding projection with each corresponding guide groove of the operating member. Therefore, the moving characteristics of each moving portion can be set by the shape of the corresponding guide groove. As a result, the degree of freedom in setting the bending of the elongated member can be enhanced with a simple configuration.

The actuating member above may further include a visual recognition portion that enables at least a bending amount of the elongated member of an advance/retraction amount and the bending amount of the elongated member to be confirmed by visual recognition.

According to this configuration, at least the bending amount, of the advance/retraction amount and the bending amount of the elongated member, can be confirmed by observing the visual recognition portion. This leads to enhanced operability of the actuating member.

In another aspect, a medical apparatus includes the actuating member as above and a flexible elongated member made by the actuating member to perform at least one of an advance/retraction action and a bending action.

According to this aspect, it is possible to provide a medical apparatus equipped with an actuating member by which an advance/retraction movement of a push/pull member can be efficiently transmitted to an elongated member and which enables a smaller medical apparatus to be realized.

BRIEF DESCRIPTION OF THE DRAWINGS

FIG. 7 is a side sectional view of an actuating member of a medical apparatus according to a Modification Example 1.

DETAILED DESCRIPTION OF THE EMBODIMENTS

Figure 1:
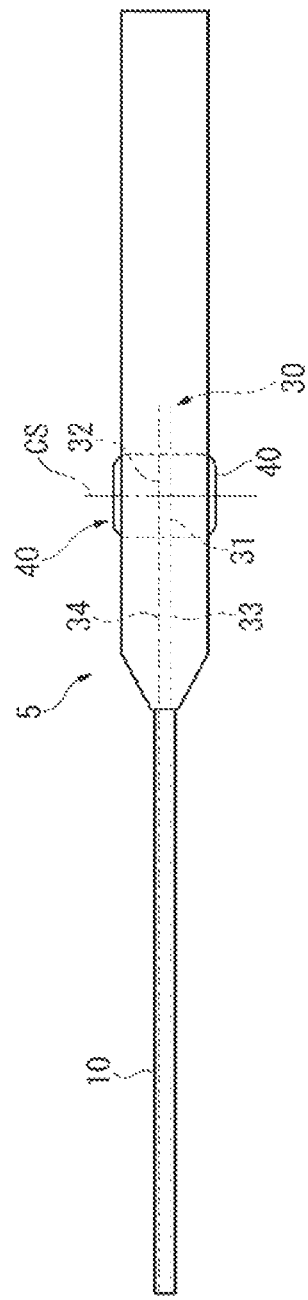
FIG. 1 is a schematic view of a medical apparatus according to a first embodiment of the present disclosure.

Preferred embodiments of the present disclosure will be described below, referring to the accompanying drawings. Note that the dimensional ratios in the drawings are exaggerated for convenience of explanation and may therefore be different from the actual ratios. In the following description, the user's proximal side of a medical apparatus according to each embodiment of the present disclosure will be referred to as the "proximal side" and the side of insertion into a body lumen or cavity will be referred to as the "distal side."

First Embodiment

The configuration of a medical apparatus 1 according to a first embodiment of the present disclosure will now be described.

Figure 2:
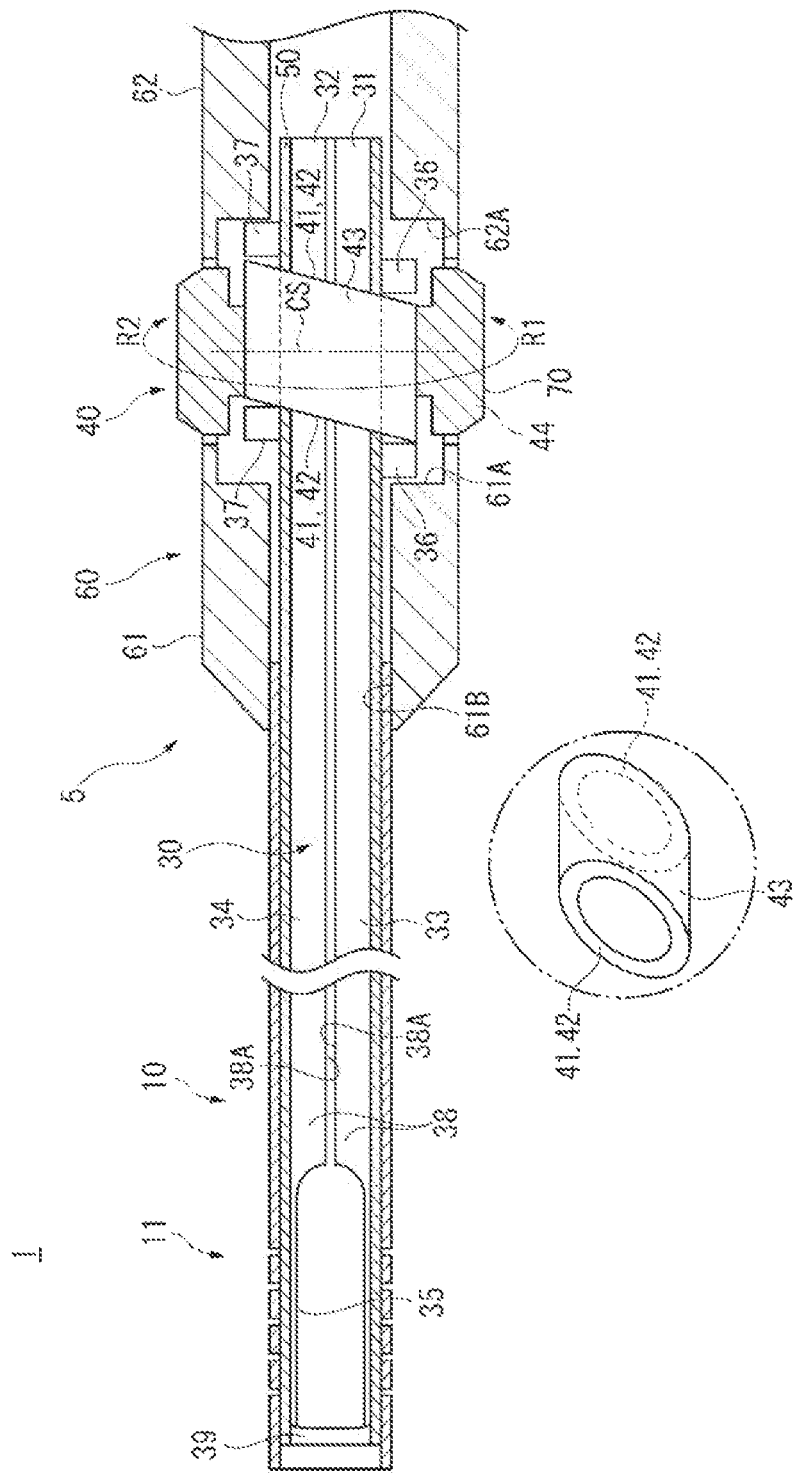
FIG. 2 is a side sectional view of the medical device according to the first embodiment.

FIG. 1 is a schematic view of the medical apparatus 1 according to the first embodiment of the disclosure, and FIG. 2 is a side sectional view of the medical apparatus 1.

As shown in FIG. 1, the medical apparatus 1 according to the first embodiment of the present disclosure includes a flexible elongated member 10 for medical use, and an actuating member 5 for making the elongated member 10 perform a predetermined action. The actuating member 5 has a push/pull member 30. The push/pull member 30 includes a plurality of divided portions 38 that will be described in more detail below. The push/pull member 30 further includes a first moving portion 31 and a second moving portion 32 that are disposed on the proximal side in an axial direction of the elongated member 10 and are movable relative to each other along the axial direction of the elongated member 10. A first extending portion 33 extends from the first moving portion 31 toward the distal side in the axial direction of the elongated member 10, and a second extending portion 34 extends from the second moving portion 32 toward the distal side in the axial direction of the elongated member 10. The push/pull member 30 is pushed/pulled in the axial direction of the elongated member 10 in conjunction with the movement of the first moving portion 31 and the second moving portion 32. The actuating member 5 further includes an operating member 40 for effecting movement of the first moving portion 31 and the second moving portion 32, the operating member 40 being rotatable in the circumferential direction of the elongated member 10. The operating member 40 includes a first guide portion, which is inclined relative to an orthogonal plane CS orthogonal to the axial direction of the elongated member 10 and which guides the movement of the first moving portion 31, and a second guide portion, which is inclined against the orthogonal plane CS and which guides the movement of the second moving portion 32. The push/pull member 30 is capable of making the elongated member 10 perform a bending action by transmitting the movement of the first moving portion 31 and the second moving portion 32, which are guided by the first guide portion and the second guide portion, to the elongated member 10. The configuration of the medical apparatus 1 will be described in detail below.

As illustrated in FIG. 2, the actuating member 5 includes the push/pull member 30, which is pushed/pulled in the axial direction of the elongated member 10 in conjunction with the movement of the first moving portion 31 and the second moving portion 32, and the operating member 40, which effects the movement of the first moving portion 31 and the second moving portion 32 and is rotatable in the circumferential direction of the elongated member 10. The actuating member 5 further includes a sealing portion 50 for sealing a fluid flowing within the push/pull member 30 and provided at the outer periphery of the push/pull member 30, a base portion 60, which supports the push/pull member 30 and the operating member 40 and which is provided at the outer periphery of the sealing portion 50, and a visual recognition portion 70, which enables the bending amount (bending angle) of the elongated member 10 to be confirmed by visual recognition.

Figure 3:
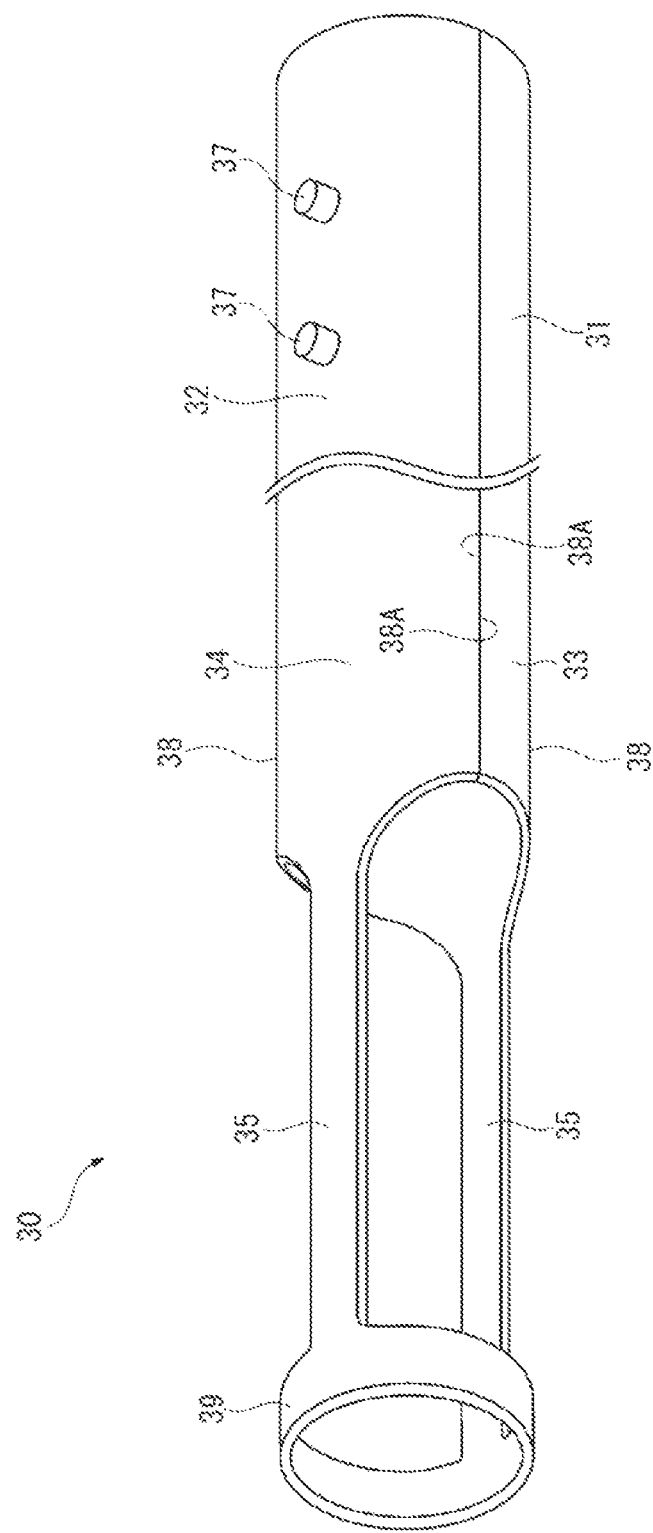
FIG. 3 is a perspective view of a push/pull member.

FIG. 3 is a perspective view of the push/pull member 30.

As depicted in FIG. 3, the push/pull member 30 includes a plurality of divided portions 38, divided in the circumferential direction and together forming a tubular structure, and an annular connecting portion 39 that connects tips of the divided portions 38. In conjunction with movement of the first moving portion 31 and the second moving portion 32, the divided portions 38 are pushed/pulled in the axial direction of the elongated member 10, thereby making the elongated member 10 perform a bending action.

The divided portions 38 include the first moving portion 31 and the second moving portion 32, which are disposed on the proximal side in the axial direction of the elongated member 10 and which are movable relative to each other along the axial direction of the elongated member 10, the first extending portion 33, which extends from the first moving portion 31 toward the distal side of the elongated member 10 in the axial direction and the second extending portion 34, which extends from the second moving portion 32 toward the distal side of the elongated member 10 in the axial direction. In addition, the divided portions 38 include bending portions 35, which are provided on the distal side of the first extending portion 33 and the second extending portion 34 and which are bent by pushing/pulling the first extending portion 33 and the second extending portion 34 relative to each other. Note that the push/pull member 30 is required only to enable the distal side of the elongated member 10 to be pushed/pulled, and may be, for example, a traction wire, a plate-shaped belt member or the like.

The first moving portion 31 has first projections 36 that project in a direction orthogonal to divided surfaces 38A of the divided portions 38. The first projections 36 are juxtaposed in the axial direction of the elongated member 10 and are provided on opposite sides of the operating member 40.

The second moving portion 32 has second projections 37 that project in a direction orthogonal to the divided surfaces 38A and opposite to the projecting direction of the first projections 36. The second projections 37 are juxtaposed in the axial direction and are provided on both sides of the operating member 40. The second projections 37 are also at positions offset toward the proximal side from positions of the first projections 36 in a state where the bending portions 35 are not bent.

The first extending portion 33 transmits movement of the first moving portion 31 to the bending portion 35.

The second extending portion 34 transmits movement of the second moving portion 32 to the bending portion 35.

Each bending portion 35 is a portion where circumferential end edges of the divided portion 38 on the distal side are cut out such that the bending portion 35 is narrower than the first extending portion 33 and the second extending portion 34.

With the push/pull member 30 configured as above, it is ensured that when the first extending portion 33 is positioned on the distal side relative to the second extending portion 34 by the movement of the first moving portion 31 and the movement of the second moving portion 32, the bending portions 35 are bent upward. When the first extending portion 33 is positioned on the proximal side relative to the second extending portion 34, the bending portions 35 are bent downward.

As shown in FIG. 2, the operating member 40 is configured so that the first moving portion 31 and the second moving portion 32 can be moved in opposite directions along the axial direction, and the movement of the first moving portion 31 and the second moving portion 32 effects a bending action of the elongated member 10. In addition, the operating member 40 includes a tubular member having a first guide surface 41 as an end surface on one side (with respect to the axial direction) constituting the first guide portion and a second guide surface 42 as an end surface on the other side constituting the second guide portion. The first guide surface 41 and the second guide surface 42 are inclined, in the same direction, relative to the orthogonal plane CS, such that movement of the first moving portion 31 and the second moving portion 32 can be effected by rotating the operating member 40. In addition, as the operating member 40 rotates, the operating member 40 causes the first moving portion 31 and the second moving portion 32 to move relative and close to each other, thereby bending the elongated member 10.

The operating member 40 includes a contact portion 43, which makes contact with the first moving portion 31 and the second moving portion 32, and an operating portion 44, which is provided on the outer peripheral surface of the contact portion 43 and which is operated directly by the user.

The contact portion 43 is formed in a hollow cylindrical shape, wherein both axial end surfaces are parallel to each other and are inclined against the orthogonal plane CS. Both end surfaces of the contact portion 43 constitute the first guide surface 41 and the second guide surface 42, which are contacted by the projections 36 and 37 located on both sides.

The operating portion 44 is formed in an annular shape, and its outer peripheral surface is exposed from the base portion 60. The operating portion 44 has its outer peripheral surface rugged so that it can be rotated by the operator's fingers.

The sealing portion 50 seals the fluid flowing within the push/pull member 30. The sealing portion 50 is fixed in close contact with the outer periphery of the push/pull member 30. The method for fixation is not particularly limited. For example, an adhesive, soldering, welding or the like, can be employed for fixation. The material constituting the sealing portion 50 may be, for example, a thermoplastic resin, which is excellent in biocompatibility. The thermoplastic resin may include fluoro-resins, such as ETFE (ethylene-tetrafluoro-ethylene copolymer), PTFE (polytetrafluoroethylene), etc., polyolefin, such as PE (polyethylene), PP (polypropylene), etc., polyamides, polyesters, polyurethane, and so on. Note that the sealing portion 50 may be disposed inside of the push/pull member 30.

The base portion 60 supports the elongated member 10, the push/pull member 30, and the operating member 40. The base portion 60 includes a support portion 61, which is disposed on the distal side relative to the operating member 40 and which supports the elongated member 10, the push/pull member 30, and the operating member 40. The base portion 60 further includes a gripping portion 62, which is disposed on the proximal side relative to the operating member 40. The gripping portion 62 supports the push/pull member 30 and the operating member 40, and is gripped by the operator when conducting a procedure. The base portion 60 may be formed of, for example, a rigid resin material or materials.

The support portion 61 supports the elongated member 10, the push/pull member 30, and the operating member 40. The support portion 61 includes a recessed portion 61A for accommodating the operating member 40 and an opening portion 61B, which is provided on the distal side and in which the elongated member 10 is inserted.

The gripping portion 62 supports the push/pull member 30 and the operating member 40, and is gripped by the operator when performing a procedure. The gripping portion 62 has a recessed portion 62A which is provided on the distal side and which accommodates the operating member 40.

The visual recognition portion 70 is provided on the outer peripheral surface of the operating member 40 and enables the bending amount of the elongated member 10 based on the movement of the first moving portion 31 and the second moving portion 32 to be confirmed by visual recognition. The visual recognition portion 70 may be, for example, a marker. However, the visual recognition portion 70 is not limited to a marker, and may be a scale or the like.

The elongated member 10 has its proximal side portion inserted in the opening portion 61B and is bent on the distal side when the bending portions 35 are bent. The elongated member 10 is provided on the distal side with rigidity-weakened portions 11 that can be easily bent. In this embodiment, the rigidity-weakened portions 11 are each configured as a combination of tubular members of a metal such as stainless steel, which is used in an endoscope or the like. While the rigidity-weakened portions 11 are provided at two parts in the vertical direction in this embodiment, it is sufficient for the rigidity-weakened portion 11 to be provided on one side. Note that the elongated member 10 may be formed from a thermoplastic resin, which is excellent in biocompatibility. The thermoplastic resin may include fluoro-resins, such as ETFE (ethylene-tetrafluoroethylene copolymer), PTFE (polytetrafluoroethylene), etc., polyolefin, such as PE (polyethylene), PP (polypropylene), etc., polyamides, polyesters, polyurethane, and so on. While the rigidity-weakened portions 11 are, for example, slits, this configuration is not restrictive, and the rigidity-weakened portions 11 may be configured by use of, for example, a material lower in rigidity than materials of other parts.

Figure 4:
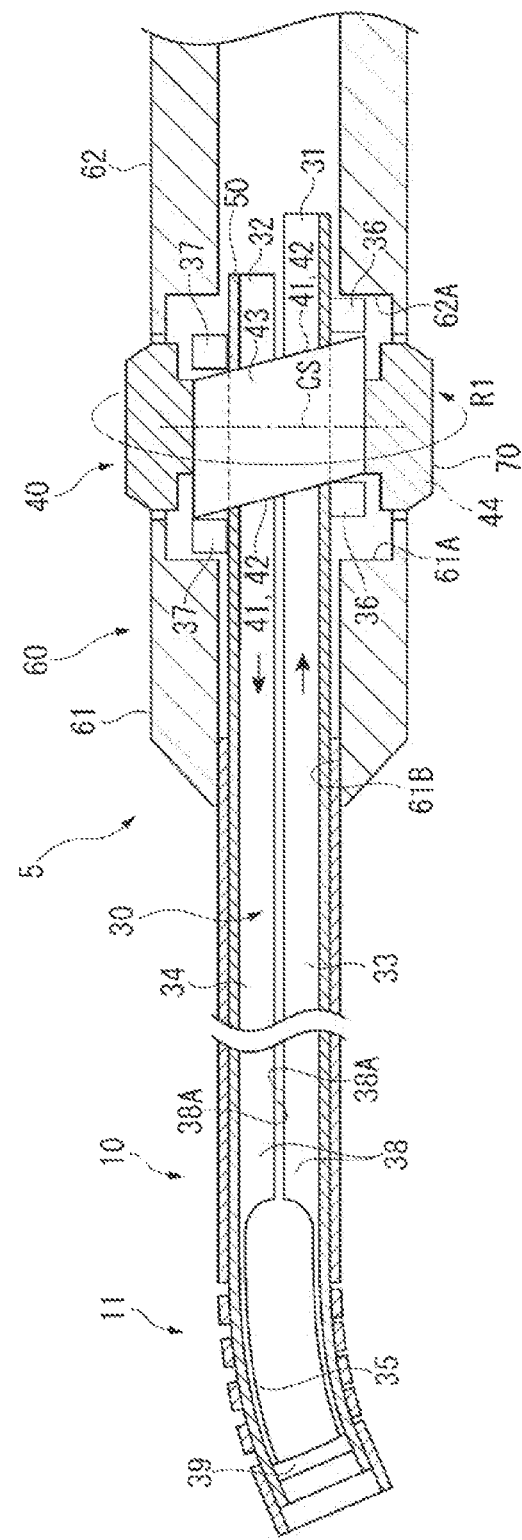
FIG. 4 is a side sectional view showing the medical apparatus in a condition where a distal side of an elongated member is bent downward in the first embodiment.

A method of bending the elongated member 10 by the actuating member 5 according to the first embodiment of the present disclosure will be described below, referring to FIG. 4. FIG. 4 is a side sectional view showing the medical apparatus 1 in a state where the distal side of the elongated member 10 is bent downward.

An operator, as shown in FIG. 4, rotates the operating member 40 in the direction of R1, for example. The first moving portion 31 is moved toward the proximal side while the first projections 36 are guided by and are in sliding contact with the first guide surface 41, whereas the second moving portion 32 is moved toward the distal side while the second projections 37 are guided by and are in sliding contact with the second guide surface 42. This moves the first extending portion 33 toward the proximal side, and moves the second extending portion 34 toward the distal side. When the first extending portion 33 is moved toward the proximal side and the second extending portion 34 is moved toward the distal side in this manner, the bending portions 35 are bent downward. When the bending portions 35 are thus bent downward, the distal side of the elongated member 10 is bent downward.

Thus, according to the first embodiment of the present disclosure, the push/pull member 30 is pushed/pulled in the axial direction of the elongated member 10, without conversion of its action direction, and the elongated member 10 is thereby made to perform a bending action. Therefore, the advance/retraction movement of the push/pull member 30 can be efficiently transmitted to the elongated member 10. Because it is unnecessary to wind the push/pull member 30 around the operating member 40, it is possible to make the medical apparatus 1 smaller in overall size.

In addition, the operating member 40 is so configured that the first moving portion 31 and the second moving portion 32 can be moved in opposite directions along the axial direction, and the bending action of the elongated member 10 is effected by moving the first moving portion 31 and the second moving portion 32. Therefore, the elongated member 10 can be bent with shorter traveling distances of the first moving portion 31 and the second moving portion 32. Accordingly, operability of the actuating member 5 is enhanced.

The moving portions 31 and 32 are moved by preliminarily setting the first projections 36 and the second projections 37 in contact with the end surfaces on one side and the other side in the axial direction of the operating member 40. Therefore, the elongated member 10 can be bent with a simple configuration, so that the medical apparatus 1 can be made smaller.

The characteristics of movement of the moving portions 31 and 32 attendant on the rotation of the operating member 40 can be set by the profile of the end surfaces of the operating member 40. Therefore, the degree of freedom in setting the bending of the elongated member 10 can be enhanced with a simple configuration.

In addition, the actuating member 5 is further provided with the visual recognition portion 70 enabling the bending amount of the elongated member 10 to be confirmed by visual recognition. Therefore, the bending amount of the elongated member 10 can be confirmed by observing the visual recognition portion 70, so that operability of the actuating member 5 is enhanced.

In addition, it is possible to provide a medical apparatus 1 equipped with the actuating member 5 by which the advance/retraction movement of the push/pull member 30 can be efficiently transmitted to the elongated member 10, and the apparatus as a whole can be made smaller.

Second Embodiment

A second embodiment of the present disclosure will be described below. In the following, descriptions of items which are common to the first and second embodiments will be omitted, and descriptions of items characteristic of only the second embodiment will be given.

Figure 5:
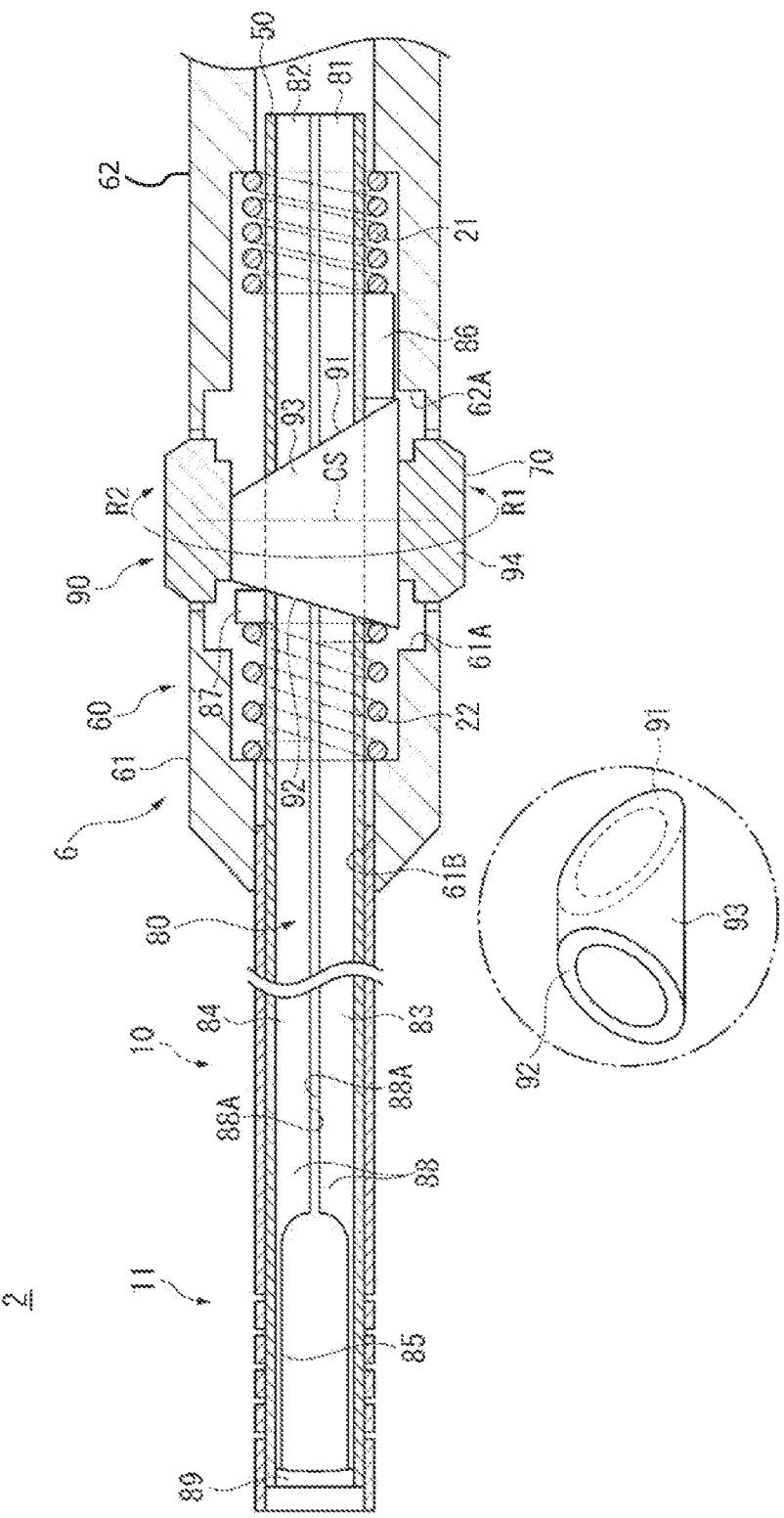
FIG. 5 is a side sectional view of a medical apparatus according to a second embodiment of the present disclosure.

FIG. 5 is a side sectional view of a medical apparatus 2 according to the second embodiment of the present disclosure.

As shown in FIG. 5, the medical apparatus 2 according to the second embodiment includes an actuating member 6. The actuating member 6 includes a push/pull member 80, which is pushed/pulled in the axial direction of an elongated member 10 in conjunction with movement of a first moving portion 81 and a second moving portion 82. The actuating member 6 further includes an operating member 90 for effecting the movement of the first moving portion 81 and the second moving portion 82 and a visual recognition portion 70, which enables the advance/retraction amount and the bending amount (bending angle) of the elongated member 10 to be confirmed by visual recognition. Note that the other configurations than the just-mentioned are the same as in the first embodiment.

The push/pull member 80 includes a plurality of divided portions 88 divided in the circumferential direction and together forming a tubular structure, and an annular connecting portion 89 interconnecting the tips of the divided portions 88 in the axial direction.

The divided portions 88 include the first moving portion 81 and the second moving portion 82, which are disposed on the proximal side of the elongated member 10 in the axial direction and which are movable relative to each other along the axial direction of the elongated member 10. The divided portion 88 also include a first extending portion 83, which extends from the first moving portion 81 toward the distal side of the elongated member 10 in the axial direction, a second extending portion 84, which extends from the second moving portion 82 toward the distal side of the elongated member 10 in the axial direction, and bending portions 85, which are provided on the distal side of the first extending portion 83 and the second extending portion 84 and which are bent by relative pushing/pulling of the first extending portion 83 and the second extending portion 84.

The first moving portion 81 has a first projection 86 projecting in a direction orthogonal to divided surfaces 88A. The first projection 86 is disposed on the proximal side of the operating member 90. The first projection 86 is biased toward the operating member 90 by a first coil spring 21 supported on a gripping portion 62.

The second moving portion 82 has a second projection 87 projecting in a direction which is orthogonal to the divided surfaces 88A and which is opposite to the projecting direction of the first projection 86. The second projection 87 is disposed on the distal side of the operating member 90. The second projection 87 is biased toward the operating member 90 by a second coil spring 22 supported on a support portion 61.

The operating member 90 is configured to be capable of moving the first moving portion 81 and the second moving portion 82, with different traveling distances, in the same direction along the axial direction, the movement of the first moving portion 81 and the second moving portion 82 causing the elongated member 10 to perform both an advance/retraction action and a bending action. In addition, the operating member 90 includes a tubular member of which a first guide surface 91 provided as an end surface on one side in the axial direction and constituting a first guide portion and a second guide surface 92 provided as an end surface on the other side in the axial direction and constituting a second guide portion are inclined, in different directions, and relative to the orthogonal plane CS. By rotating the operating member 90, movement of the first moving portion 81 and the second moving portion 82 is effected. Attendant on its rotation, the operating member 90 relatively moves the first moving portion 81 and the second moving portion 82 away from each other, thereby bending the elongated member 10.

The operating member 90 includes a contact portion 93 and an operating portion 94.

The contact portion 93 is formed in a hollow cylindrical shape, such that an end surface on the proximal side in the axial direction is inclined against the orthogonal plane CS, and an end surface on the distal side is also inclined against the orthogonal plane CS, but toward the opposite side and at a different angle as compared with the inclination of the proximal side end surface. The proximal side end surface is greater than the distal side end surface in inclination angle relative to the orthogonal plane CS. The proximal side end surface of the contact portion 93 constitutes the first guide surface 91, and the first projection 86 engages with the first guide surface 91. Similarly, the distal side end surface of the contact portion 93 constitutes the second guide surface 92, and the second projection 87 engages with the second guide surface 92.

Figure 6:
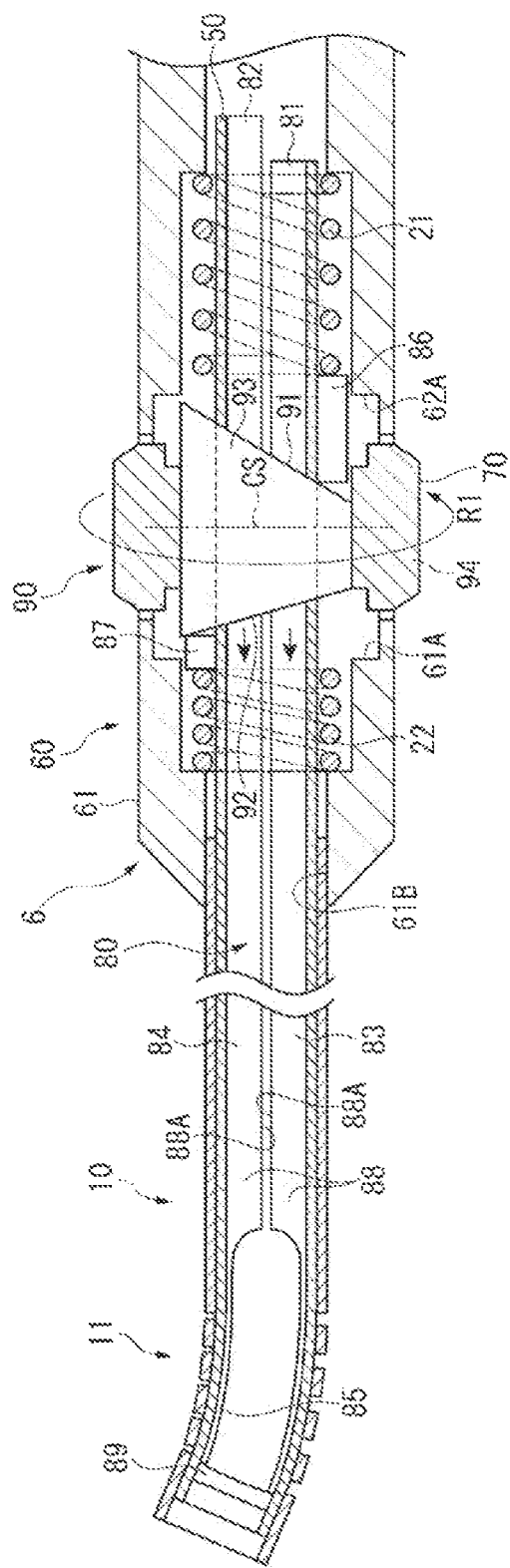
FIG. 6 is a side sectional view showing the medical apparatus in a condition where a distal side of an elongated member is bent upward in the second embodiment.

A method of bending the distal side of the elongated member 10 by the actuating member 6 according to the second embodiment of the present disclosure will be described below, referring to FIG. 6. FIG. 6 is a side sectional view showing the medical apparatus 2 in a condition where the distal side of the elongated member 10 is bent upward.

As shown in FIG. 6, the operator rotates the operating member 90 in the direction of R1. This causes the first moving portion 81 to move toward the distal side while being guided by the first guide surface 91, and also causes the second moving portion 82 to move toward the distal side while being guided by the second guide surface 92. In this case, since the inclination angle of the first guide surface 91 is greater than the inclination angle of the second guide surface 92 relative to the orthogonal plane CS, the first moving portion 81 moves farther toward the distal side than the second moving portion 82. Therefore, the bending portions 85 are bent upward while being moved toward the distal side. When the bending portions 85 are bent upward while being moved toward the distal side, the distal side of the elongated member 10 is bent upward while the elongated member 10 is moved toward the distal side.

Thus, according to the second embodiment of the present disclosure, the push/pull member 80 is pushed/pulled in the axial direction of the elongated member 10, without conversion of its action direction, and the elongated member 10 is thereby made to perform both an advance/retraction action and a bending action. Therefore, the advance/retraction movement of the push/pull member 80 can be efficiently transmitted to the elongated member 10. In addition, because it is unnecessary to wind the push/pull member 80 around the operating member 90, it is possible to make the medical apparatus 2 smaller in overall size.

The operating member 90 is configured to be capable of moving the first moving portion 81 and the second moving portion 82 with different traveling distances, in the same direction along the axial direction. The movement of the first moving portion 81 and the second moving portion 82 makes the elongated member 10 perform an advance/retraction action and a bending action. Therefore, an actuating member 6 with enhanced performance can be provided.

Now, modifications of the above embodiments will be described below by way of examples.

FIG. 7 and FIGS. 8A to 11B are side sectional views of actuating members 5A to 5E of medical apparatuses according to Modification Examples 1 to 5. Note that in FIG. 7 and FIGS. 8A to 11B, other configurations than the actuating members 5A to 5E are omitted.

Modification Example 1

An actuating member 5A of a medical apparatus 1A shown in FIG. 7 includes a push/pull member 80, and first and second coil springs 21 and 22, which makes this modification example different from the first embodiment.

In the push/pull member 80, a first projection 86 is disposed on the proximal side of an operating member 40, and is biased toward the operating member 40 by the first coil spring 21.

A second projection 87 is disposed on the distal side of the operating member 40, and is biased toward the operating member 40 by the second coil spring 22.

According to this configuration, when the operating member 40 is rotated, an elongated member 10 is bent, like in the first embodiment. Specifically, when a first moving portion 81 is moved toward the proximal side and a second moving portion 82 is moved toward the distal side, bending portions 85 are bent downward, whereby the distal side of the elongated member 10 is bent downward.

Modification Example 2

Figure 8A:
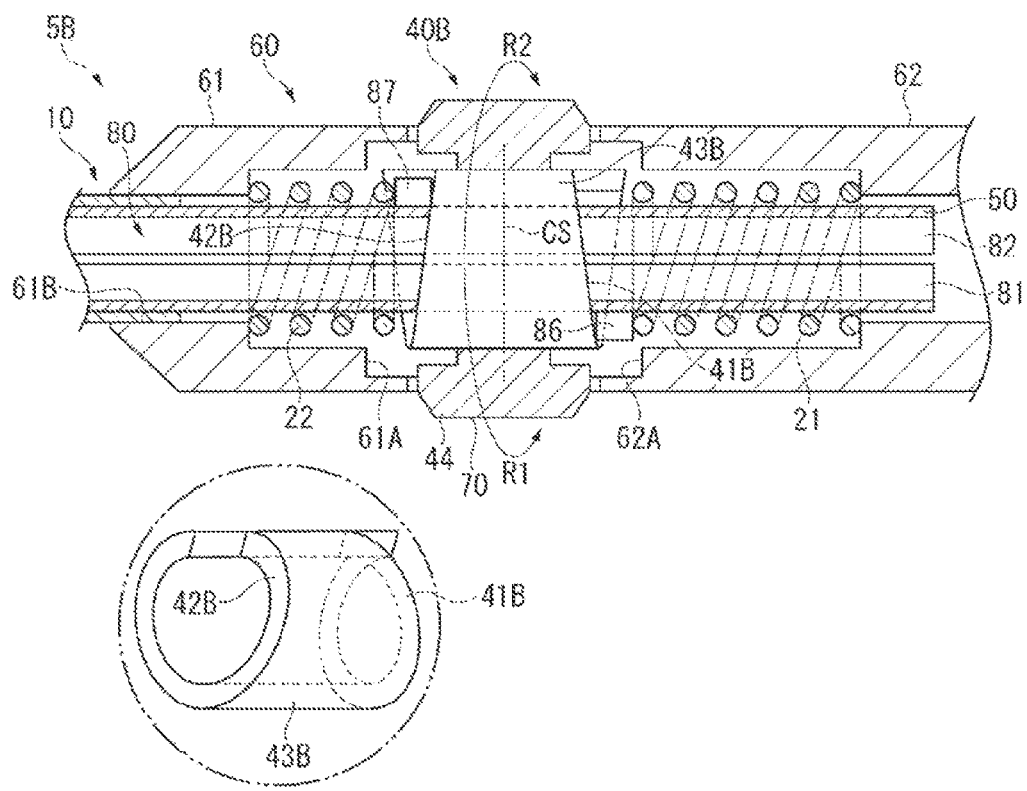
FIGS. 8A and 8B are side sectional views of an actuating member of a medical apparatus according to a Modification Example 2.

An actuating member 5B shown in FIG. 8A includes a push/pull member 80 and an operating member 40B, which makes this modification example different from the first embodiment.

The operating member 40B includes a contact portion 43B and an operating portion 44.

Of the contact portion 43B, an end surface on the proximal side is formed in a spiral shape such as to advance toward the distal side when rotated clockwise as viewed from the proximal side. On the other hand, an end surface on the distal side is formed in a spiral shape such as to advance toward the proximal side when rotated counterclockwise as viewed from the distal side. The proximal side end surface of the contact portion 43B constitutes a first guide surface 41B, whereas the distal side end surface of the contact portion 43B constitutes a second guide surface 42B.

Figure 8B:
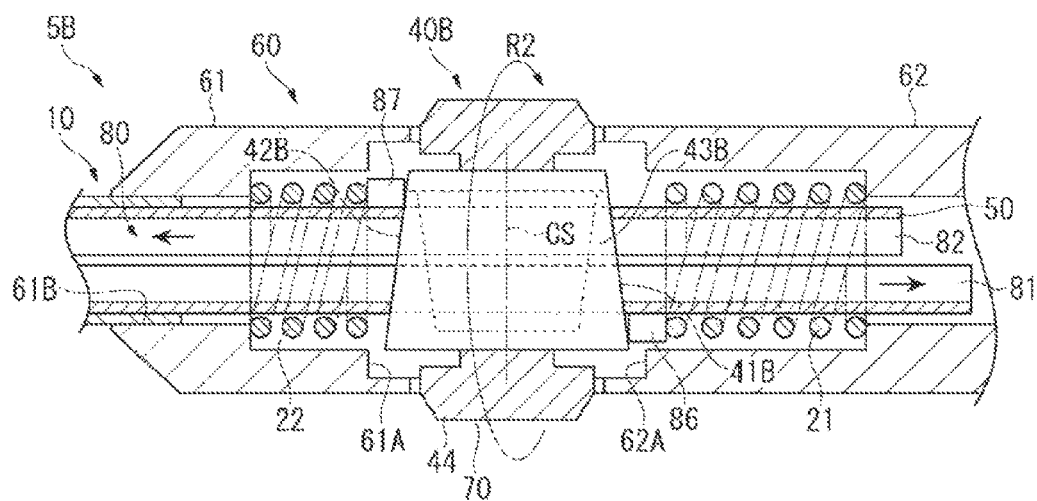

According to this configuration, when the operating member 40B is rotated in the direction of R2, a first moving portion 81 is moved toward the proximal side, while a second moving portion 82 is moved toward the distal side, as shown in FIG. 8B, so that the distal side of an elongated member 10 is bent downward.

Modification Example 3

Figure 9A:
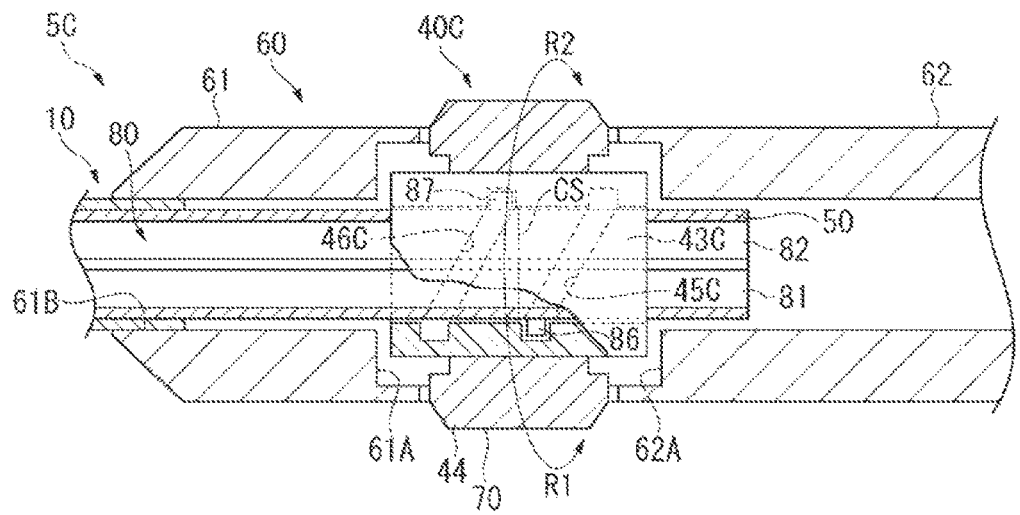
FIGS. 9A and 9B are side sectional views of an actuating member of a medical apparatus according to a Modification Example 3.

An actuating member 5C shown in FIG. 9A includes a push/pull member 80 and an operating member 40C, which makes this modification example different from the first embodiment.

The operating member 40C includes a tubular member, which has an inner peripheral surface provided with a first guide groove 45C constituting a first guide portion and with a second guide groove 46C constituting a second guide portion. The operating member 40C includes a contact portion 43C and an operating portion 44.

The inner peripheral surface of the contact portion 43C is provided with the first guide groove 45C and the second guide groove 46C in annular shapes which are inclined, toward the same side, relative to the orthogonal plane CS and which are parallel to each other. A first projection 86 engages with the first guide groove 45C, whereas a second projection 87 engages with the second guide groove 46C.

Figure 9B:
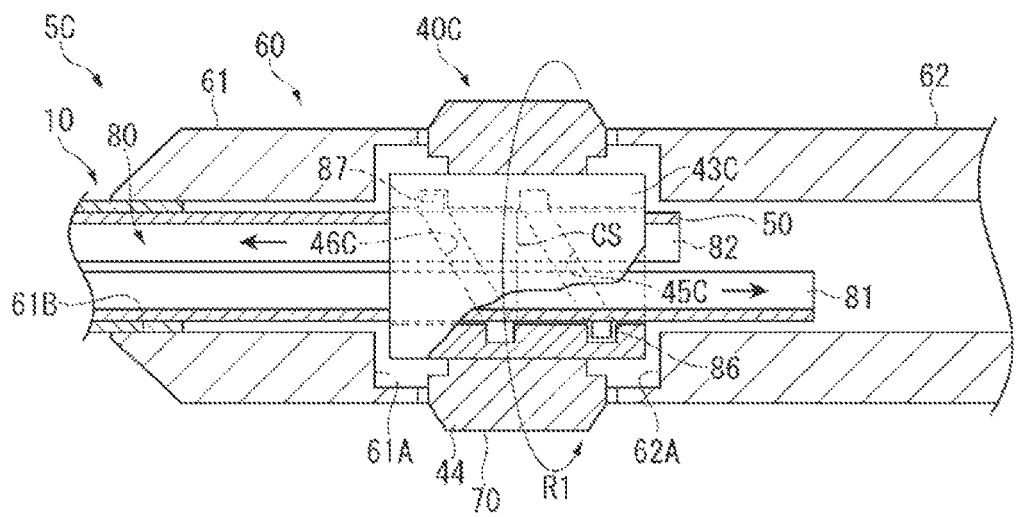

This configuration ensures that when the operating member 40C is rotated in the direction of R1, for example, a first moving portion 81 is moved toward the proximal side, with the first projection 86 guided by and in sliding contact with the first guide groove 45C, as illustrated in FIG. 9B. In addition, a second moving portion 82 is moved toward the distal side, with the second projection 87 guided by and in sliding contact with the second guide groove 46C. As a result, bending portions are bent downward, whereby the distal side of an elongated member 10 is bent downward.

In addition, the moving portions 81 and 82 are moved through preliminary engagement of the first projection 86 and the second projection 87 respectively with the first guide groove 45C and the second guide groove 46C which are formed on the inner peripheral surface of the operating member 40C. Therefore, the elongated member 10 can be bent by means of a simple configuration, and a medical apparatus equipped with this actuating member 5C can be made smaller.

Further, moving characteristics of the moving portions 81 and 82 can be set by the shapes of the guide grooves 45C and 46C. Consequently, the degree of freedom in setting the bending of the elongated member 10 can be enhanced with a simple configuration.

Modification Example 4

Figure 10A:
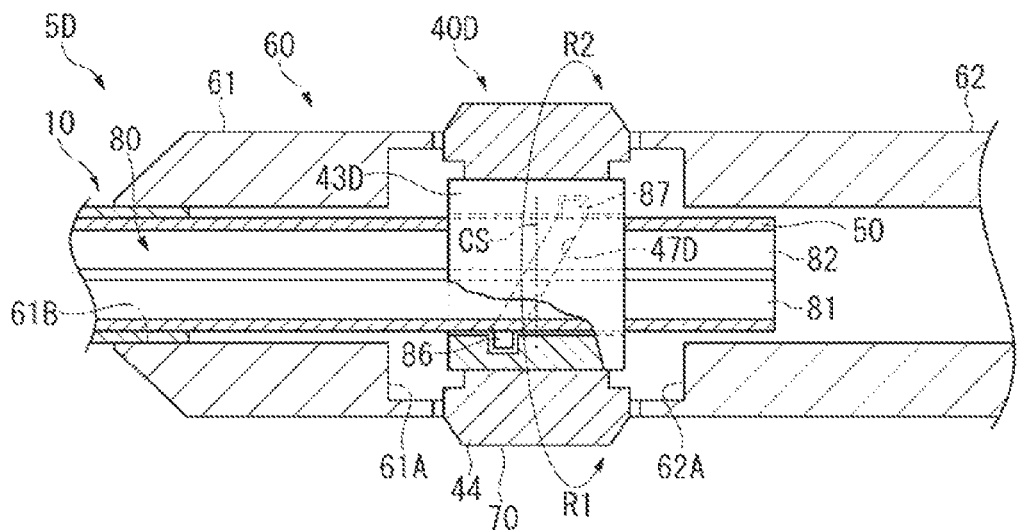
FIGS. 10A and 10B are side sectional views of an actuating member of a medical apparatus according to a Modification Example 4.

An actuating member 5D shown in FIG. 10A includes a push/pull member 80 and an operating member 40D, which makes this modification example different from the first embodiment.

The operating member 40D includes a contact portion 43D and an operating portion 44.

An inner peripheral surface of the contact portion 43D is formed with a guide groove 47D as a first guide portion and a second guide portion. The guide groove 47D is formed in an annular shape that is inclined against the orthogonal plane CS. A first projection 86 and a second projection 87 engage with the guide groove 47D.

Figure 10B:
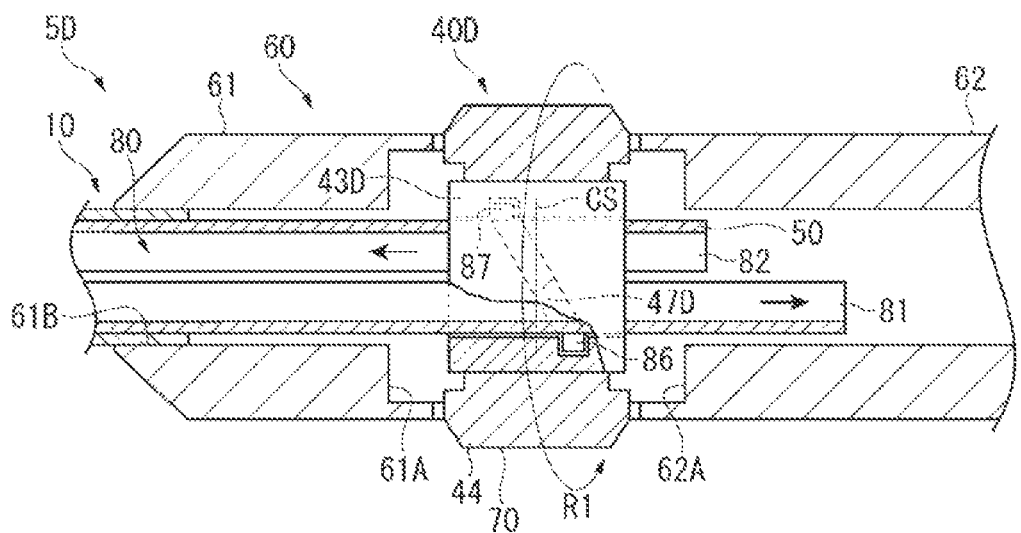

According to this configuration, when the operating member 40D is rotated in the direction of R1, for example, a first moving portion 81 is moved toward the proximal side whereas a second moving portion 82 is moved toward the distal side, as illustrated in FIG. 10B. As a result, bending portions are bent downward, and the distal side of an elongated member 10 is bent downward.

Modification Example 5

Figure 11A:
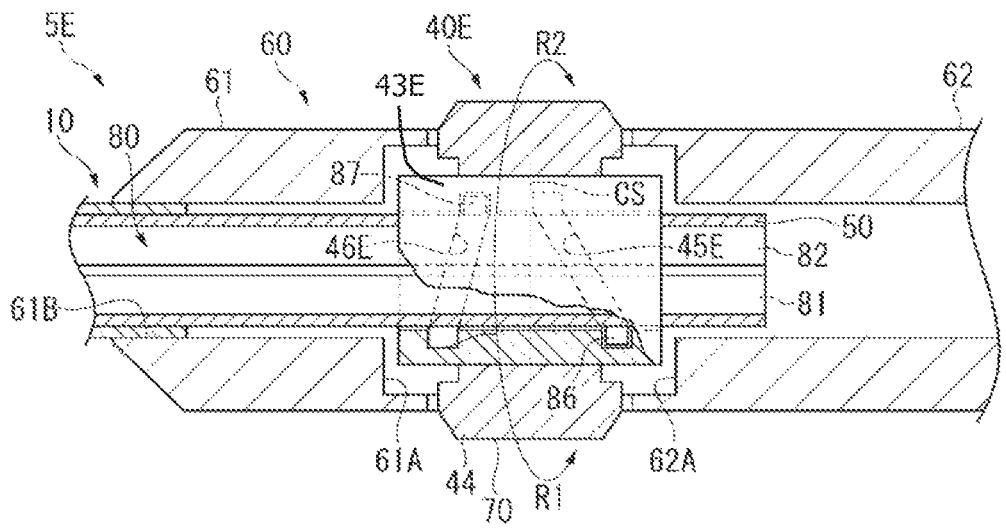
FIGS. 11A and 11B are side sectional views of an actuating member of a medical apparatus according to a Modification Example 5.

An actuating member 5E shown in FIG. 11A includes a push/pull member 80 and an operating member 40E, which makes this modification example different from the first embodiment.

The operating member 40E includes a tubular member, which has an inner peripheral surface formed with a first guide groove 45E constituting a first guide portion and a second guide groove 46E constituting a second guide portion. The operating member 40E includes a contact portion 43E and an operating portion 44.

An inner peripheral surface of the contact portion 43E is provided with the first guide groove 45E and the second guide groove 46E in annular shapes which are inclined, toward different sides, relative to the orthogonal plane CS. The inclination angle of the first guide groove 45E is greater than the inclination angle of the second guide groove 46E relative to the orthogonal plane CS. A first projection 86 engages with the first guide groove 45E, whereas a second projection 87 engages with the second guide groove 46E.

Figure 11B:
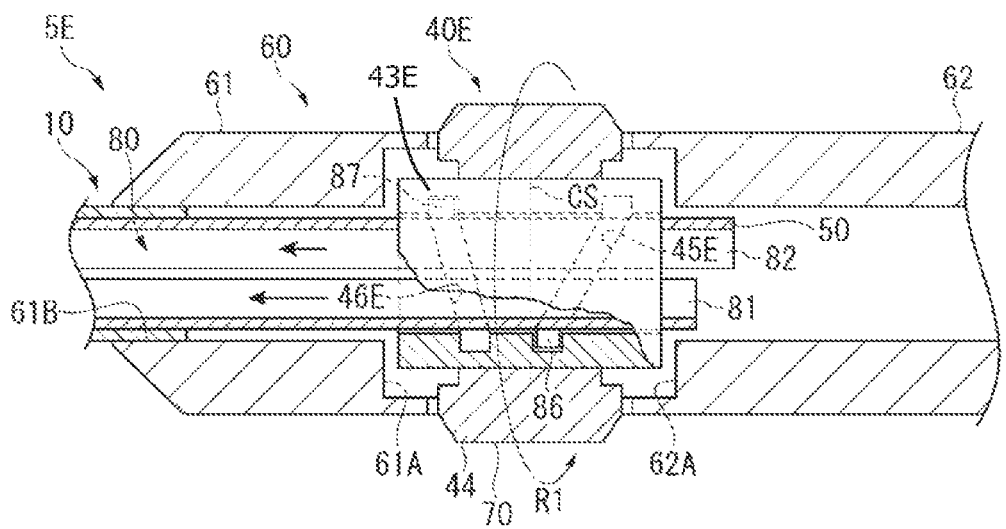

This configuration ensures that when the operating member 40E is rotated in the direction of R1, for example, a first moving portion 81 and a second moving portion 82 are both moved toward the distal side, as illustrated in FIG. 11B. In this case, because the inclination angle of the first guide groove 45E is greater than the inclination angle of the second guide groove 46E relative to the orthogonal plane CS, the traveling distance of the first moving portion 81 is greater than the traveling distance of the second moving portion 82. Therefore, bending portions are bent upward while moving toward the distal side. Consequently, the distal side of an elongated member 10 is bent upward while the elongated member 10 is moved toward the distal side.

Note that the present disclosure is not limited to the aforementioned embodiments and modification examples, and that various changes, improvements, and the like, could be effected therein by one skilled in the art without departing from the spirit and scope of the disclosure as defined in the appended claims.

For instance, a configuration may be adopted wherein the first moving portion 31 or 81 is provided with the first guide groove, whereas the second moving portion 32 or 82 is provided with the second guide groove, and the operating member is provided with the first projection and the second projection. In addition, a configuration may be adopted wherein the first moving portion 31 or 81 is provided with the first guide groove, whereas the second moving portion 32 or 82 is provided with the second projection, and the operating member is provided with the first projection and the second groove. Alternatively, a configuration may be adopted wherein the first moving portion 31 or 81 is provided with the first projection, whereas the second moving portion 32 or 82 is provided with the second groove, and the operating member is provided with the first guide groove and the second projection. In addition, the operating member may be provided with the first guide groove and the second guide surface, or may be provided with the first guide surface and the second guide groove. Moreover, both the first projection and the second projection may be put into contact with an end surface on one side or the other side of the operating member in the axial direction.

Furthermore, the guide surfaces 41, 41B, 42, 42B, 91 and 92 and the guide grooves 45C, 45E, 46C, 46E and 47D may have any shape so long as they can move the first moving portion 31 or 81 and the second moving portion 32 or 82 along the axial direction of the elongated member 10. By suitably setting the shapes of the guide surfaces 41, 41B, 42, 42B, 91 and 92 and the guide grooves 45C, 45E, 46C, 46E and 47D, it is possible to arbitrarily set the moving characteristics of the moving portions 31, 32, 81 and 82 in response to the rotation of the operating member 40, 40B, 40C, 40D, 40E or 90, and to precisely set the moving characteristics of the moving portions 31, 32, 81 and 82.

In addition, the first projection 36 or 86 and the second projection 37 or 87 may be provided not only in the direction orthogonal to the divided surfaces 38A or 88A of the first moving portion 31 or 81 and the second moving portion 32 or 82, but also at any position in the circumferential direction of the divided portions 38 or 88. In addition, these projections may be provided for the first moving portion 31 or 81 and the second moving portion 32 or 82 through additional members, or may be disposed in agreement with the major axis of the elongated member 10.

Further, each of the guide grooves 45C, 45E, 46C, 46E and 47D may be formed to penetrate the operating member 40C, 40D or 40E.

The operating member 40, 40B, 40C, 40D, 40E or 90 may be operated for rotation directly by hand, or may be operated for rotation through a slidable additional member.

The push/pull member 30 or 80 may not have the connecting portion 39 or 89. In this case, the elongated member 10 can be bent by adopting a construction wherein distal side end portions in the axial direction of the elongated member 10 of the bending portions 35 or 85 are connected to the elongated member 10.

In addition, for the elongated member 10, there can be adopted any configuration that enables the elongated member 10 to perform a bending action.

The push/pull member 30 or 80 may not have the sealing portion 50. In this case, a treatment instrument can be inserted into and passed through a lumen defined by the push/pull member 30 or 80 from the proximal side of the base portion 60. As a result, in a body lumen or cavity, a part on the distal side as compared with the connecting portion 39 can be treated.

The present disclosure is applicable not only to medical apparatuses for use in diagnosis or treatment of paranasal sinus but also to any other medical apparatus that has a bendable elongated body.

It should be understood by those skilled in the art that various modifications, combinations, sub-combinations and alterations may occur depending on design requirements and other factors insofar as they are within the scope of the appended claims or the equivalents thereof.

What is claimed is:
1. An actuating member for making a flexible elongated member for medical use perform a predetermined action, the actuating member comprising:
    a push/pull member comprising:
        a first moving portion and a second moving portion that are disposed on a proximal side in an axial direction of the elongated member and that are movable relative to each other in the axial direction of the elongated member, a first extending portion that extends from the first moving portion toward a distal side in the axial direction of the elongated member, and
a second extending portion that extends from the second moving portion toward the distal side in the axial direction of the elongated member,
wherein the first moving portion includes one or more first projections, and the second moving portion includes one or more second projections, and
wherein the push/pull member is configured to be pushed and pulled in the axial direction of the elongated member in conjunction with a movement of the first moving portion and the second moving portion; and
an operating member configured to effect the movement of the first moving portion and the second moving portion, the operating member being rotatable in a circumferential direction of the elongated member,
wherein the operating member comprises:
an annular member that includes:
a first end surface at an overall proximal end of the annular member, the first end surface facing at least in part in a proximal direction,
a second end surface at an overall distal end of the annular member, the second end surface facing at least in part in a distal direction,
an outer peripheral surface extending from an outer peripheral edge of the first end surface to an outer peripheral edge of the second end surface, and
an inner peripheral surface extending from an inner peripheral edge of the first end surface to an inner peripheral edge of the second end surface,
wherein each of the first end surface and the second end surface is inclined relative to an orthogonal plane that is orthogonal to the axial direction of the elongated member,
wherein the first end surface of the annular member is configured to guide movement of the first moving portion by contacting at least one of the one or more first projections upon rotation of the operating member, and
wherein the second end surface of the annular member is configured to guide movement of the second moving portion by contacting at least one of the one or more second projections upon rotation of the operating member, and
wherein the push/pull member is configured to make the elongated member perform at least one of (i) an advance/retraction action and (ii) a bending action, by transmitting the movement of the first moving portion and the second moving portion, which are guided by the first end surface and the second end surface, to the elongated member.

2. The actuating member according to claim 1, wherein the operating member is configured to move the first moving portion and the second moving portion in opposite axial directions, and the movement of the first moving portion and the second moving portion makes the elongated member perform the bending action.

3. The actuating member according to claim 1, wherein the operating member is configured to move the first moving portion and the second moving portion in the same axial direction with different traveling distances, and the movement of the first moving portion and the second moving portion makes the elongated member perform both the advance/retraction action and the bending action.

4. The actuating member according to claim 1, wherein the one or more first projections include a proximal first projection and a distal first projection,
wherein the one or more second projections include a proximal second projection and a distal second projection,
wherein the first end surface of the annular member is configured to guide movement of the first moving portion by contacting the proximal first projection,
wherein the second end surface of the annular member is configured to guide movement of the first moving portion by contacting the distal first projection,
wherein the first end surface of the annular member is configured to guide movement of the second moving portion by contacting the proximal second projection, and
wherein the second end surface of the annular member is configured to guide movement of the second moving portion by contacting the distal second projection.

5. The actuating member according to claim 1, wherein a direction in which the first end surface is inclined is opposite a direction in which the second end surface is inclined.

6. The actuating member according to claim 1, wherein the push/pull member is configured to make the elongated member perform at least the bending action, and
wherein the actuating member further comprising a visual recognition portion that enables at least a bending amount of the elongated member to be confirmed by visual recognition.

7. The actuating member according to claim 6, wherein the visual recognition portion comprises a marker or a scale.

8. A medical apparatus comprising:
the actuating member according to claim 1; and
a flexible elongated member, wherein the actuating member is configured to make the flexible elongated member perform at least one of the advance/retraction action and the bending action.

9. An actuating member for making a flexible elongated member for medical use perform a predetermined action, the actuating member comprising:
a push/pull member comprising:
a first moving portion and a second moving portion that are disposed on a proximal side in an axial direction of the elongated member and that are movable relative to each other in the axial direction of the elongated member,
a first extending portion that extends from the first moving portion toward a distal side in the axial direction of the elongated member, and
a second extending portion that extends from the second moving portion toward the distal side in the axial direction of the elongated member,
wherein the first moving portion includes a first projection, and the second moving portion includes a second projection, and
wherein the push/pull member is configured to be pushed and pulled in the axial direction of the elongated member in conjunction with a movement of the first moving portion and the second moving portion; and
an operating member configured to effect the movement of the first moving portion and the second moving portion, the operating member being rotatable in a circumferential direction of the elongated member,
wherein the operating member comprises:
a tubular member that includes:
a first guide groove and a second guide groove formed in an inner peripheral surface of the tubular member,
wherein the first guide groove and the second guide groove are disposed such that, in side cross-sectional view of the tubular member, the first guide groove and the second guide groove do not intersect,
wherein the first projection is located in the first guide groove, and the second projection is located in the second guide groove,
wherein the first guide groove of the annular member is configured to guide movement of the first moving portion by contacting the first projection upon rotation of the operating member, and
wherein the second guide groove of the annular member is configured to guide movement of the second moving portion by contacting the second projection upon rotation of the operating member, and
wherein the push/pull member is configured to make the elongated member perform at least one of (i) an advance/retraction action and (ii) a bending action, by transmitting the movement of the first moving portion and the second moving portion, which are guided by the first guide groove and the second guide groove, to the elongated member.

10. The actuating member according to claim 9, wherein the first guide groove and the second guide groove are inclined toward the same side relative to an orthogonal plane that is orthogonal to the axial direction of the elongated member, and
wherein the operating member is configured to move the first moving portion and the second moving portion in opposite axial directions, and the movement of the first moving portion and the second moving portion makes the elongated member perform the bending action.

11. The actuating member according to claim 9, wherein the first guide groove and the second guide groove are inclined toward different sides relative to an orthogonal plane that is orthogonal to the axial direction of the elongated member, and
wherein the operating member is configured to move the first moving portion and the second moving portion in the same axial direction with different traveling distances, and the movement of the first moving portion and the second moving portion makes the elongated member perform both the advance/retraction action and the bending action.

12. The actuating member according to claim 9, wherein the push/pull member is configured to make the elongated member perform at least the bending action, and
wherein the actuating member further comprising a visual recognition portion that enables at least a bending amount of the elongated member to be confirmed by visual recognition.

13. The actuating member according to claim 12, wherein the visual recognition portion comprises a marker or a scale.

14. A medical apparatus comprising:
the actuating member according to claim 9; and
a flexible elongated member, wherein the actuating member is configured to make the flexible elongated member perform at least one of the advance/retraction action and the bending action.

15. An actuating member for making a flexible elongated member for medical use perform a predetermined action, the actuating member comprising:
a push/pull member comprising:
a first moving portion and a second moving portion that are disposed on a proximal side in an axial direction of the elongated member and that are movable relative to each other in the axial direction of the elongated member,
a first extending portion that extends from the first moving portion toward a distal side in the axial direction of the elongated member, and
a second extending portion that extends from the second moving portion toward the distal side in the axial direction of the elongated member,
wherein the first moving portion includes a first projection, and the second moving portion includes a second projection, and
wherein the push/pull member is configured to be pushed and pulled in the axial direction of the elongated member in conjunction with a movement of the first moving portion and the second moving portion; and
an operating member configured to effect the movement of the first moving portion and the second moving portion, the operating member being rotatable in a circumferential direction of the elongated member,
wherein the operating member comprises:
a tubular member that includes:
exactly one guide groove formed in an inner peripheral surface of the tubular member,
wherein the exactly one guide groove is inclined relative to an orthogonal plane that is orthogonal to the axial direction of the elongated member,
wherein the first projection and second projections are both located in the exactly one guide groove,
wherein the exactly one guide groove of the annular member is configured to guide movement of the first moving portion and the second moving portion by contacting the first and second projections upon rotation of the operating member, and
wherein the push/pull member is configured to make the elongated member a bending action by transmitting the movement of the first moving portion and the second moving portion, which are guided by the exactly one guide groove, to the elongated member.

16. The actuating member according to claim 15, wherein the operating member is configured to move the first moving portion and the second moving portion in opposite axial directions.

17. The actuating member according to claim 15, wherein the actuating member further comprising a visual recognition portion that enables at least a bending amount of the elongated member to be confirmed by visual recognition.

18. The actuating member according to claim 17, wherein the visual recognition portion comprises a marker or a scale.

19. A medical apparatus comprising:
the actuating member according to claim 15; and
a flexible elongated member, wherein the actuating member is configured to make the flexible elongated member perform at least one of the advance/retraction action and the bending action.

* * * * *